United States Patent
Doyle (10) Patent No.: US 8,752,549 B2
(45) Date of Patent: Jun. 17, 2014

(54) AIRWAY PRESSURE RELEASE VENTILATION

(75) Inventor: Peter Raymond Doyle, Vista, CA (US)

(73) Assignee: Koninklijke Philips N.V., Eindhoven (NL)

( * ) Notice: Subject to any disclaimer, the term of this patent is extended or adjusted under 35 U.S.C. 154(b) by 372 days.

(21) Appl. No.: 13/133,186

(22) PCT Filed: Nov. 18, 2009

(86) PCT No.: PCT/IB2009/055150
§ 371 (c)(1),
(2), (4) Date: Jun. 7, 2011

(87) PCT Pub. No.: WO2010/067224
PCT Pub. Date: Jun. 17, 2010

(65) Prior Publication Data
US 2011/0232644 A1 Sep. 29, 2011

Related U.S. Application Data

(60) Provisional application No. 61/121,226, filed on Dec. 10, 2008.

(51) Int. Cl.
*F16K 31/02* (2006.01)
*A61M 16/00* (2006.01)
*A62B 7/00* (2006.01)

(52) U.S. Cl.
USPC .................................. 128/204.23

(58) Field of Classification Search
USPC .............. 128/203.14, 204.18, 204.21–204.23
See application file for complete search history.

(56) References Cited

U.S. PATENT DOCUMENTS

| | | | |
|---|---|---|---|
| 5,353,788 A | 10/1994 | Miles | |
| 5,385,142 A * | 1/1995 | Brady et al. | 128/204.23 |
| 6,609,517 B1 * | 8/2003 | Estes et al. | 128/204.23 |
| 6,988,498 B2 * | 1/2006 | Berthon-Jones et al. | 128/204.23 |
| 2003/0111078 A1* | 6/2003 | Habashi | 128/204.18 |
| 2005/0241639 A1* | 11/2005 | Zilberg | 128/204.21 |
| 2006/0249149 A1* | 11/2006 | Meier et al. | 128/204.18 |
| 2008/0000475 A1* | 1/2008 | Hill | 128/204.18 |
| 2008/0295839 A1* | 12/2008 | Habashi | 128/204.22 |

FOREIGN PATENT DOCUMENTS

| WO | 9945989 A1 | 9/1999 |
|---|---|---|
| WO | 2008148134 A1 | 4/2008 |
| WO | 2008146264 A1 | 12/2008 |

* cited by examiner

*Primary Examiner* — Kristen Matter (57) ABSTRACT

A pressure support system (50) and method includes delivering a first flow of gas (D) to the patient having first and second positive pressure levels that alternate with one another in a plurality of first cycles. The first flow of gas has a first period that is different than a predetermined apnea period. The method includes determining that the patient is experiencing an apneic episode, and, in response, delivering a second flow of gas to the patient. The second flow of gas has the first and second positive pressure levels that alternate with one another in a plurality of second cycles in the second flow of gas. The second flow of gas has a second period that is equal to the predetermined apnea period.

18 Claims, 7 Drawing Sheets

AIRWAY PRESSURE RELEASE VENTILATION

BACKGROUND OF THE INVENTION

1. Field of the Invention

The present invention relates to a positive airway pressure support system for providing airway pressure release ventilation (APRV), and, more particularly, to a positive pressure support system and method of providing positive pressure support in an APRV mode that provides a back-up form of ventilation for use during episodes, such as episodes of apnea, where the patient stops breathing.

2. Description of the Related Art

Pressure support ventilation systems that provide a flow of breathing gas to an airway of a patient at an elevated pressure to treat a medical disorder are well known. One type of known pressure support ventilation is airway pressure release ventilation (APRV). APRV is a mode of medical ventilation that is often used to treat patients with acute lung injury. In APRV mode, a flow of breathing gas, such as air, is provided to a patient's airway at two different, alternating positive pressure levels (often referred to as PEEP High and PEEP Low) to provide ventilation and lung inflation while allowing the patient to spontaneously breath at both pressure levels.

The particular PEEP High and PEEP Low levels and the relative duration of each (i.e., the frequency of the changes from HIGH to LOW and back) are all parameters that are determined by the health care provider based on the particular therapy needs of the patient. For example, a patient may be placed on an APRV therapy wherein the PEEP High duration (referred to as "Time High") is longer than the PEEP Low duration (referred to as "Time Low") in order to facilitate ventilation while maintaining lung expansion. This is the more common type of APRV therapy that is provided. However, in some situations, particularly when a patient has less of a need for PEEP High lung inflation strategies, the patient may be placed on an APRV therapy wherein the Time High is shorter than the Time Low.

In current ventilators that provide APRV therapy (or a similar therapy that allows patients to breath spontaneously at two PEEP levels), if the patient becomes apneic (i.e., stops breathing), an apnea alarm is sounded and, in some ventilators, a back-up apnea ventilation mode is invoked. The settings for the back-up apnea ventilation mode are established by the clinician and do not attempt to preserve the initial intention of the base ventilator settings specific to APRV. In particular, in most current back-up apnea ventilation modes, the Time High ventilation is replaced with a fixed tidal volume or pressure at a relatively short inspiratory time. In situations where Time High is relatively long, this may not provide an adequate mean airway pressure for the patient due to the loss of the relatively long PEEP High setting.

SUMMARY OF THE INVENTION

In one embodiment, the invention provides a method of providing pressure support to a patient that includes delivering a first flow of breathing gas to the patient, wherein the first flow of breathing gas has a first positive pressure level and a second positive pressure level, wherein the first and second positive pressure levels alternate with one another in a plurality of first cycles in the first flow of breathing gas, and wherein the first flow of breathing gas has a first period that is different than a predetermined apnea period (e.g., based on a predetermined apnea rate set by a clinician). The method further determining that the patient is experiencing an apneic episode (e.g., based on not detecting any breaths during a predetermined apnea interval), and, in response to the determining, delivering a second flow of breathing gas to the patient, wherein the second flow of breathing gas has the first positive pressure level and the second positive pressure level, wherein the first and second positive pressure levels alternate with one another in a plurality of second cycles in the second flow of breathing gas, and wherein the second flow of breathing gas has a second period that is equal to the predetermined apnea period.

In another embodiment, a pressure support system is provided that includes a pressure generating system, a patient circuit operatively coupled to the pressure generating system, and a controller operatively coupled to the pressure generating system. The controller is adapted to: (i) control the pressure generating system to deliver a first flow of breathing gas to the patient through the patient circuit, the first flow of breathing gas having a first positive pressure level and a second positive pressure level, the first and second positive pressure levels alternating with one another in a plurality of first cycles in the first flow of breathing gas, the first flow of breathing gas having a first period that is different than a predetermined apnea period, (ii) determine that the patient is experiencing an apneic episode, and (iii) in response to determining that the patient is experiencing an apneic episode, control the pressure generating system to deliver a second flow of breathing gas to the patient, the second flow of breathing gas having the first positive pressure level and the second positive pressure level, the first and second positive pressure levels alternating with one another in a plurality of second cycles in the second flow of breathing gas, the second flow of breathing gas having a second period that is equal to the predetermined apnea period.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DESCRIPTION OF THE PREFERRED EMBODIMENTS

As employed herein, the statement that two or more parts or components are "coupled" together shall mean that the parts are joined or operate together either directly or through one or more intermediate parts or components. As also employed herein, the term "number" shall mean one or an integer greater than one (i.e., a plurality).

The present invention, in the various embodiments described herein, provides a positive pressure support system and a method of providing positive pressure support in an APRV mode (or a similar mode that allows patients to breath spontaneously at two PEEP levels) that includes an apnea back-up mode that utilizes much of the currently applied APRV settings while still ensuring adequate apnea back-up ventilation. The present invention also contemplates that the therapy method including apnea back-up as described herein in various embodiments is implemented in a microprocessor (or similar controller)-based pressure support system that includes hardware to allow the microprocessor (or similar controller) to control the ventilation (i.e., the provision of breathing gas at specified pressures) as described in greater detail herein.

In addition, the present invention further contemplates that the microprocessor (or similar controller)-based pressure support system will allow a clinician (or a patient at the direction of the clinician) to set: (i) an apnea interval, and (ii) an apnea rate for use as described herein once apnea has been declared. The apnea interval is a predetermined time interval wherein, if no triggered breaths have been sensed during the interval, apnea is declared. As described in greater detail herein, when an apnea is declared, the apnea back-up ventilation mode is invoked. The apnea rate is a specified number of full ventilation cycles (which correspond to patient breathing cycles) per specified time duration (e.g., one minute), wherein each full ventilation cycle is characterized by a high pressure period followed by a low pressure period. Thus, as will be appreciated, the apnea rate will also define the period of each individual cycle (referred to herein as the "apnea period"), which is the time duration of the cycle (measured, for example, from the beginning of the high pressure to the end of the low pressure of the cycle). For instance, the apnea rate may be set to be equal to 15 cycles (breaths) per minute. The apnea period for such an apnea rate would thus be 4 seconds. As described in greater detail herein, the apnea rate is used to control the particulars of the ventilation provided during the apnea back-up ventilation mode. Specifically, the apnea back-up ventilation mode in the various embodiments described herein provides back-up ventilation wherein the particular PEEP High and PEEP Low levels of the original APRV mode are maintained and are provided at the pre-set apnea rate.

Figure 1:
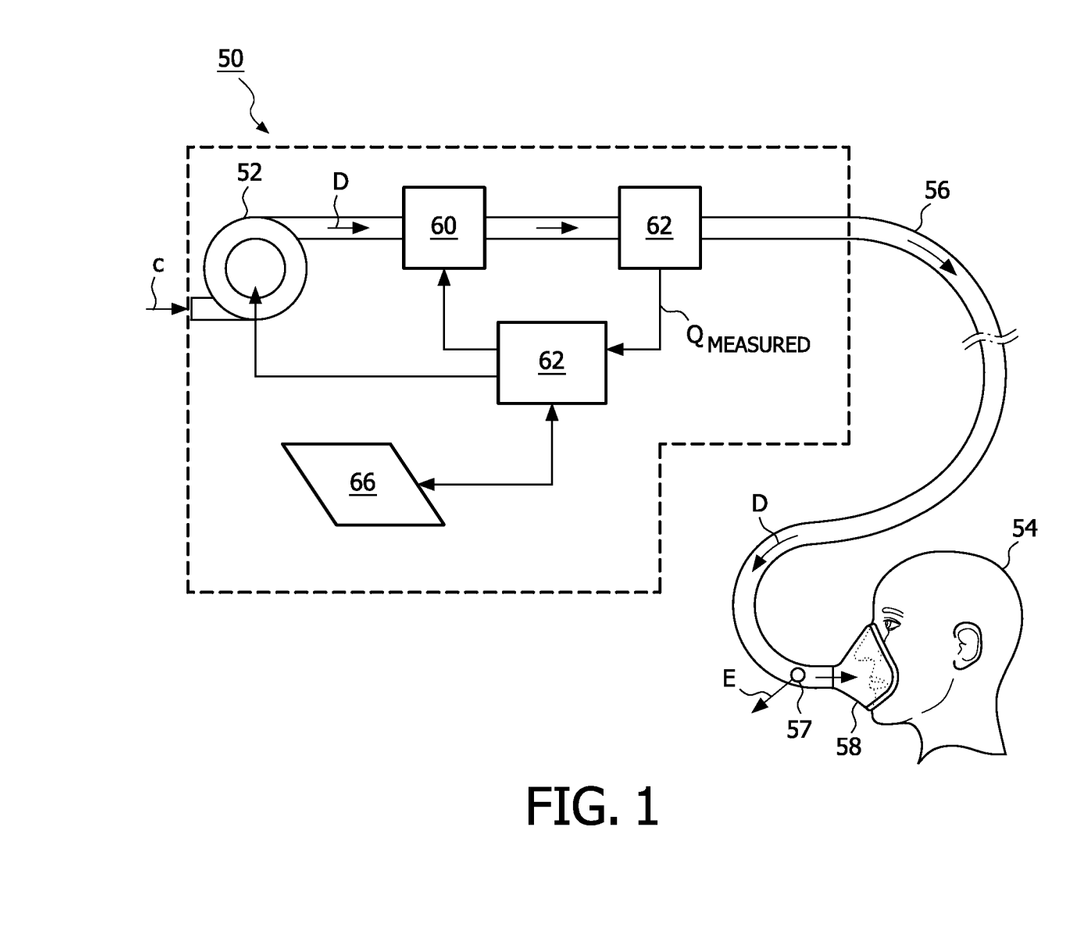
FIG. 1 is a schematic diagram of a pressure support system for providing positive pressure support in an APRV or similar mode that includes an apnea back-up mode according to one particular, non-limiting embodiment of the invention.

FIG. 1 is a schematic diagram of a pressure support system 50 for providing positive pressure support in an APRV mode (or a similar mode that allows patients to breath spontaneously at two PEEP levels) that includes an apnea back-up mode (as described in greater detail herein) according to one particular, non-limiting embodiment of the invention. Referring to FIG. 1, pressure support system 50 includes a gas flow generator 52, such as a blower used in a conventional CPAP or bi-level pressure support device, that receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of a patient 54 at relatively higher and lower pressures. The pressurized flow of breathing gas, generally indicated by arrow D from gas flow generator 52, is delivered via a delivery conduit 56 to a breathing mask or patient interface 58 of any known construction, which is typically worn by or otherwise attached to the patient to communicate the flow of breathing gas to the airway of the patient 54. Delivery conduit 56 and patient interface device 58 are typically collectively referred to as a patient circuit.

Pressure support system 50 shown in FIG. 1 is what is known as a single-limb system, meaning that the patient circuit includes only a delivery conduit 56 connecting the patient to pressure support system 50. As such, an exhaust vent 57 is provided in delivery conduit 56 for venting exhaled gasses from the system as indicated by arrow E. It should be noted that exhaust vent 57 can be provided at other locations in addition to or instead of in delivery conduit 56, such as in patient interface device 58. It should also be understood that exhaust vent 57 can have a wide variety of configurations depending on the desired manner in which gas is to be vented from the pressure support system 50.

The present invention also contemplates that the pressure support system 50 can be a two-limb system, having a delivery conduit and an exhaust conduit connected to the patient 54. In a two-limb system, the exhaust conduit carries exhaust gas from the patient 54 and includes an exhaust valve at the end distal from the patient. A two-limb system is typically referred to as a ventilator.

Furthermore, in the illustrated exemplary embodiment of the present invention shown in FIG. 1, patient interface 58 is a nasal/oral mask. It is to be understood, however, that patient interface 58 can include a nasal/oral mask, nasal pillows, tracheal tube, endotracheal tube, or any other device that provides a suitable gas flow communicating function. Also, for purposes of the present invention, the phrase "patient interface" can include delivery conduit 56 and any other structures that connects the source of pressurized breathing gas to the patient.

In the illustrated embodiment, pressure support system 50 includes a pressure controller in the form of a valve 60 provided in delivery conduit 56. Valve 60 controls the pressure of the flow of breathing gas from flow generator 52 delivered to patient 54. For present purposes, flow generator 52 and valve 60 are collectively referred to as a pressure generating system because they act in concert to control the pressure and/or flow of gas delivered to the patient. However, it should be apparent that other techniques for controlling the pressure of the gas that is delivered to the patient, such as varying the blower speed of flow generator 52, either alone or in combination with a pressure control valve, are contemplated by the present invention. Thus, valve 60 is optional depending on the technique used to control the pressure of the flow of breathing gas delivered to the patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes a flow sensor 62 that measures the flow of the breathing gas within delivery conduit 56. In the particular embodiment shown in FIG. 1, flow sensor 62 is interposed in line with delivery conduit 56, for example, downstream of valve 60. Flow sensor 62 generates a flow signal $Q_{MEASURED}$ that is provided to a controller 64 and is used by controller 64 to determine the flow of gas at patient 54.

Of course, other techniques for measuring the respiratory flow of the patient 54 are contemplated by the present invention, such as, without limitation, measuring the flow directly at patient 54 or at other locations along delivery conduit 56, measuring patient flow based on the operation of flow generator 52, and measuring patient flow using a flow sensor upstream of valve 60.

Controller 64 may be, for example, a microprocessor, a microcontroller or some other suitable processing device, that includes or is operatively coupled to a memory (not shown) that provides a storage medium for data and software executable by controller 64 for controlling the operation of pressure support system 50, including controlling the flow of breathing gas to provide ventilation to the patient in an APRV mode and to implement the apnea back-up mode of operation in the various embodiments described in detail elsewhere herein. Finally, an input/output device 66 is provided for setting various parameters used by pressure support system 50, as well as for displaying and outputting information and data to a user, such as a clinician or caregiver.

Figure 2A:
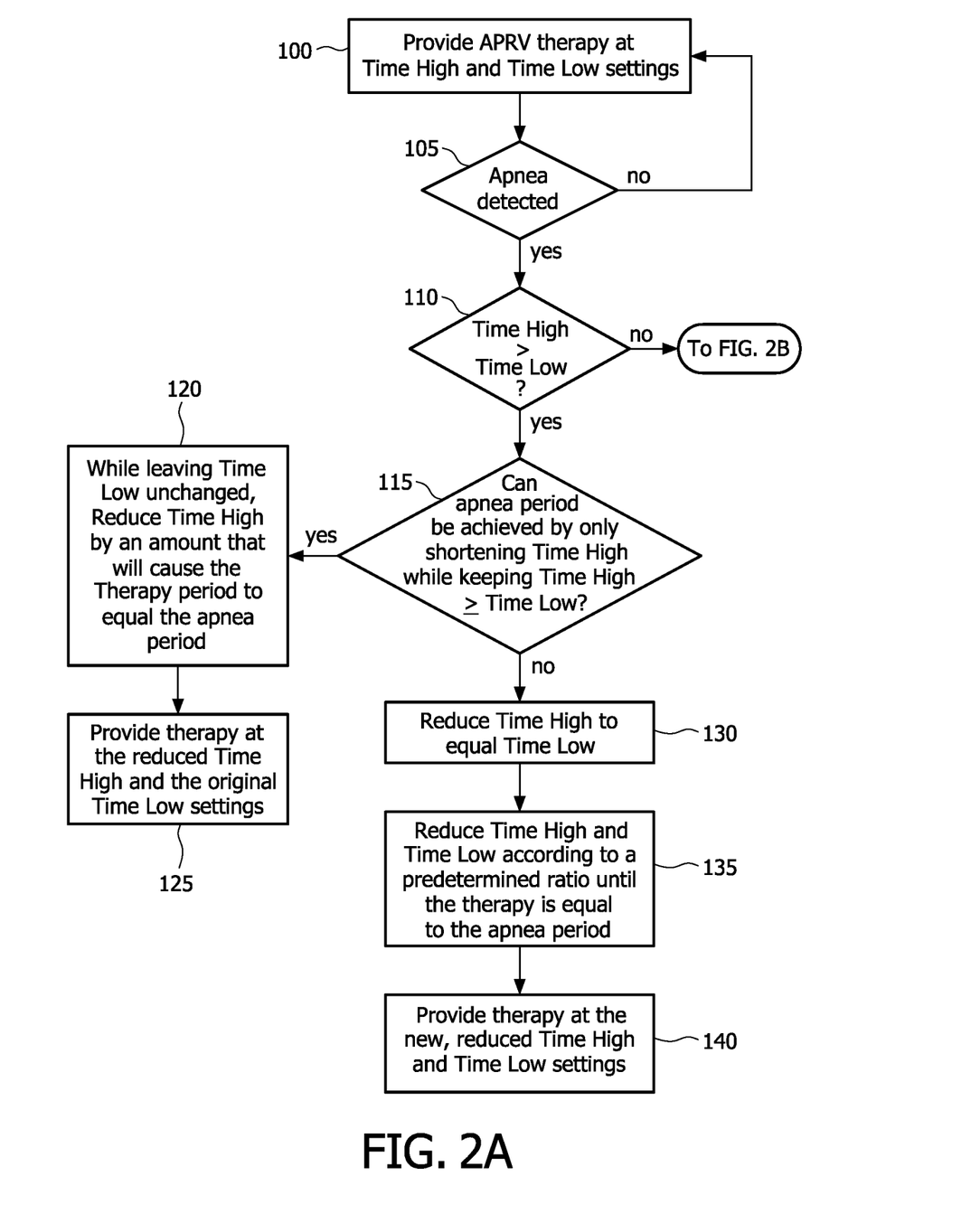
FIGS. 2A and 2B are a flowchart of a method of providing apnea back-up ventilation according to one particular, non-limiting embodiment of the invention.
Figure 2B:
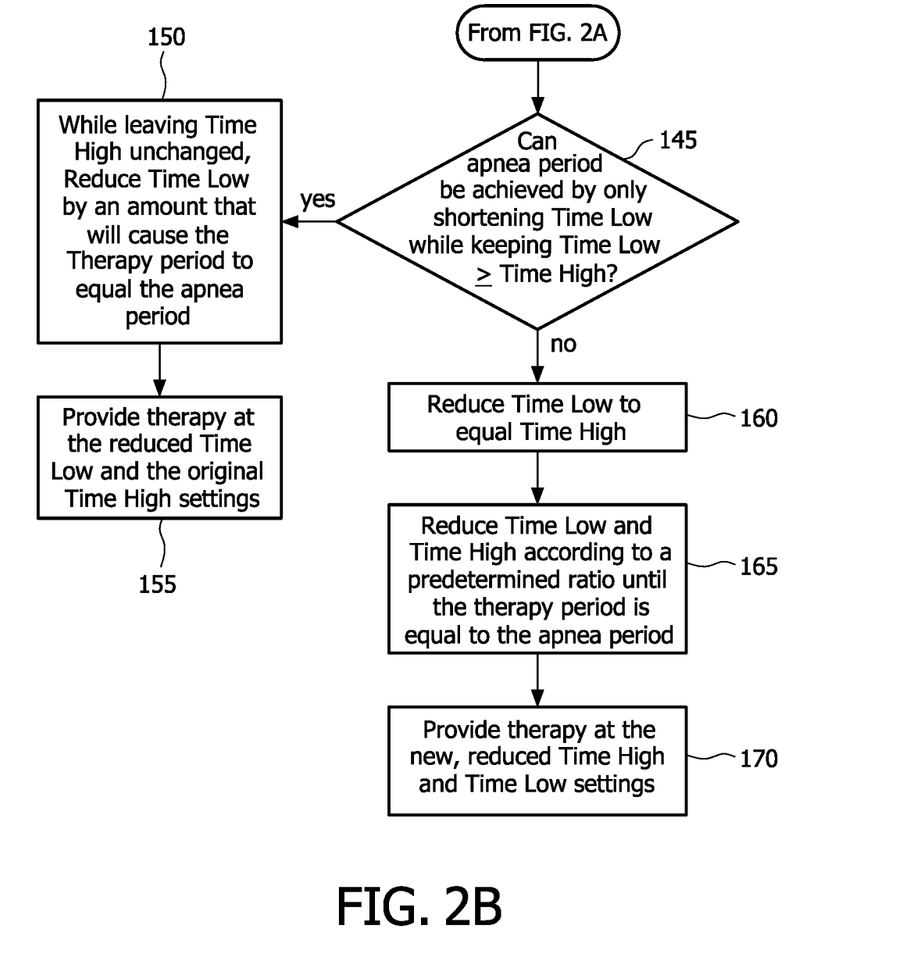

FIGS. 2A and 2B are a flowchart of a method of providing apnea back-up ventilation using pressure support system 50 according to one particular, non-limiting embodiment of the invention. The method begins at step 100, wherein APRV therapy is provided to the patient 54 at predetermined PEEP High/Time High and PEEP Low/Time Low settings. Such settings may be established and input into pressure support system 50 using the input/output device 66. Next, at step 105, a determination is made as to whether apnea (i.e., an episode of suspension of respiration) is detected based on the pre-set apnea interval. Specifically, step 105 determines whether no triggered breaths have been sensed during the pre-set apnea interval. Triggered breaths may be sensed by pressure support system 50 using any suitable known or hereafter developed method. For example, as is known in the art, triggered breaths may be sensed by pressure support system 50 using the $Q_{MEASURED}$ signal that is provided to controller 64. If the answer at step 105 is no, meaning that apnea has not been detected, then the method returns to step 100, where the original APRV therapy is continued.

If, however, the answer at step 105 is yes, meaning that apnea has been detected, then, at step 110, a determination is made as to whether Time High is greater than Time Low. If the answer is yes, then the method proceeds to step 115. At step 115, a determination is made as to whether the ventilation therapy can be adjusted so as to be provided at the apnea period while maintaining the original PEEP High and PEEP Low pressure levels by only shortening the Time High (and not changing the Time Low) while keeping Time High greater than or equal to Time Low. If the answer is yes, then the method proceeds to step 120. At step 120, while leaving Time Low unchanged, Time High is reduced by an amount that will cause the therapy period (the period of the ventilation therapy provided to the patient) to equal the apnea period. Then, at step 125, therapy is provided at the original PEEP High and PEEP Low pressure levels at the reduced Time High setting and the original Time Low setting.

If the answer at step 115 is no, meaning that the apnea period cannot be achieved by only shortening the Time High while keeping Time High greater than or equal to Time Low, then, at step 130, Time High is reduced to be equal to Time Low. Then, at step 135, Time High and Time Low are reduced according to a predetermined ratio until the therapy period is equal to the apnea period. In one particular embodiment, the predetermined ratio is 1:1, so that Time High and Time Low are reduced by equal amounts until the therapy period is equal to the apnea period. This will prevent inverting the I:E factor during apnea ventilation.

In another, alternative particular embodiment, the predetermined ratio is equal to the ratio of original Time High to original Time Low. Thus, in this embodiment, Time High and Time Low are reduced proportionally until the therapy period is equal to the apnea period. These specific ratios are meant to be exemplary only, and it will be understood that other ratios may be used and may be selectively set by a clinician or the patient as desired using the input/output device 66 of the pressure support system 50. Following step 135, the method proceeds to step 140, wherein therapy is provided at the original PEEP High and PEEP Low pressure levels at the new reduced Time High setting and the new reduced Time Low setting.

Returning to step 110, if the answer is no, meaning that Time Low is greater than or equal to Time High, then the method proceeds to step 145 in FIG. 2B. At step 145, a determination is made as to whether the ventilation therapy can be adjusted so as to be provided at the apnea period while maintaining the original PEEP High and PEEP Low pressure levels by only shortening the Time Low (and not changing the Time High) while keeping Time Low greater than or equal to Time High. If the answer is yes, then the method proceeds to step 150. At step 150, while leaving Time High unchanged, Time Low is reduced by an amount that will cause the therapy period (the period of the ventilation therapy provided to the patient) to equal the apnea period. Then, at step 155, therapy is provided at the original PEEP High and PEEP Low pressure levels at the reduced Time Low setting and the original Time High setting.

If the answer at step 145 is no, meaning that the apnea period cannot be achieved by only shortening the Time Low while keeping Time Low greater than or equal to Time High, then, at step 160, Time Low is reduced to be equal to Time High. Then, at step 165, Time Low and Time High are reduced according to a predetermined ratio (as described elsewhere herein; e.g., 1:1 or original Time Low:original Time High) until the therapy period is equal to the apnea period. Following step 165, the method proceeds to step 170, wherein therapy is provided at the original PEEP High and PEEP Low pressure levels at the new reduced Time High setting and the new reduced Time Low setting.

Thus, in the particular, non-limiting embodiment shown in FIGS. 2A and 2B, if possible, the apnea rate/period is achieved by only shortening the longer of the original Time High and the original Time Low. If that is not possible, then the longer one is reduced to equal the shorter one, and then both are reduced (according to the predetermined ratio) to achieve the apnea rate/period.

In an alternative embodiment, at step 130, rather than reducing Time High to be equal to Time Low, Time High is reduced until the ratio of Time High to Time Low reaches a predetermined value. Thereafter, the method proceeds to step 135, where both Time High and Time Low are reduced as described herein, by equal amounts (ratio of 1:1). Similarly, in this embodiment, at step 160, rather than reducing Time Low to be equal to Time High, Time Low is reduced until the ratio of Time Low to Time High reaches a predetermined value. Thereafter, the method proceeds to step 165, where both Time Low and Time High are reduced as described herein, by equal amounts (ratio of 1.1).

Figure 3A:
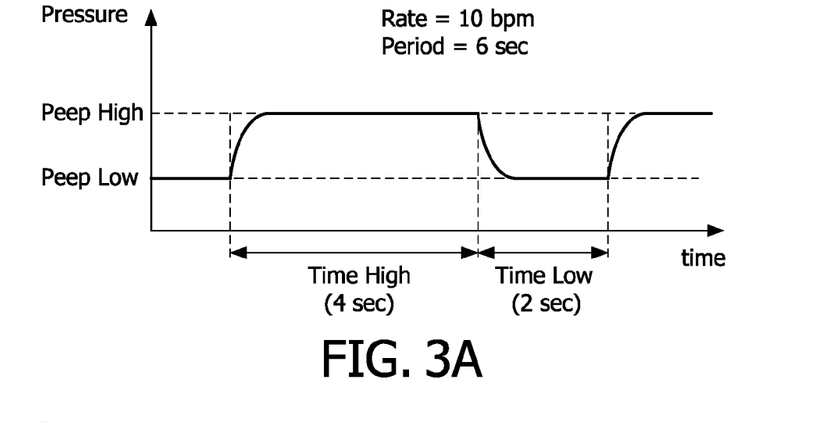
FIGS. 3A, 3B, and 3C and FIGS. 4A, 4B, and 4C show various example pressure curves for therapy provided according to the method of FIGS. 2A and 2B.
Figure 3B:
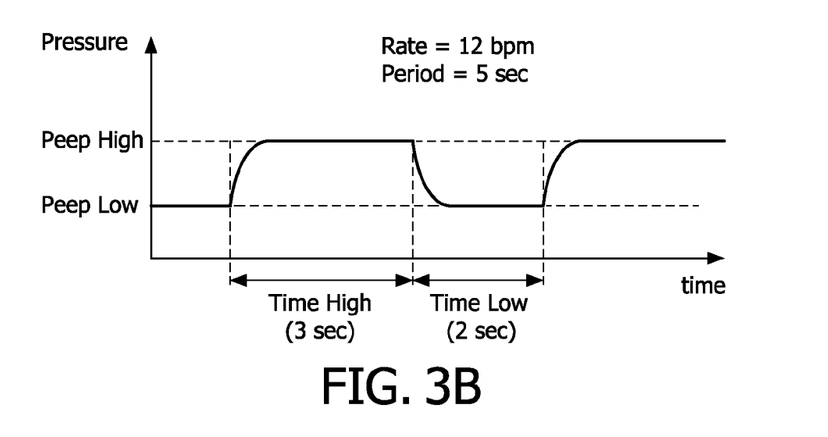

FIGS. 3A, 3B, and 3C and FIGS. 4A, 4B, and 4C show various example pressure curves for therapy provided according to the method of FIGS. 2A and 2B. FIG. 3A shows example APRV therapy provided by pressure support system 50 in a case where Time High equals 4 seconds, Time Low equals 2 seconds, the respiratory rate is 10 bpm, and the respiratory period is 6 seconds. In this example, Time High is greater than Time Low, and therefore, when apnea is detected, processing will proceed in accordance with steps 115-140 in FIG. 2A. FIG. 3B illustrates the apnea back-up mode that will follow the therapy shown in FIG. 3A when the predetermined apnea back-up rate is set to 12 bpm, resulting in an apnea period of 5 seconds. As seen in FIG. 3B, when apnea is detected, it is possible to achieve the apnea period of 5 seconds by only shortening Time High of FIG. 3A. Thus, in the apnea back-up mode shown in FIG. 3B, Time High is shortened to 3 seconds, and Time Low is unchanged, resulting in a back-up therapy at the apnea rate/apnea period wherein the particular PEEP High and Low levels of the original APRV mode are maintained (see steps 120 and 125 of FIG. 2A).

Figure 3C:
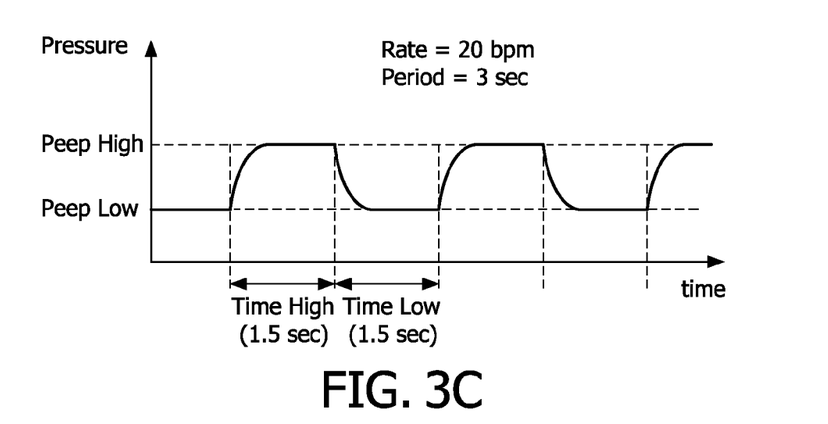

FIG. 3C illustrates the apnea back-up mode that will follow the therapy shown in FIG. 3A when the predetermined apnea back-up rate is set to 20 bpm, resulting in an apnea period of 3 seconds. As seen in FIG. 3C, when apnea is detected, it is not possible to achieve the apnea period of 3 seconds by only shortening Time High of FIG. 3A while keeping Time High greater than or equal to Time Low. Thus, in this case, Time High is first reduced to 2 seconds to make it equal to Time Low. Then, both Time High and Time Low are reduced by 0.5 seconds so that each equals 1.5 seconds. This will result in a back-up therapy at the apnea rate/apnea period wherein the particular PEEP High and Low levels of the original APRV mode are maintained (see steps 130, 135 and 140 of FIG. 2A). Also, Time High, which was originally longer than Time Low, will remain at least greater than or equal to Time Low in the back-up therapy that is provided.

Figure 4A:
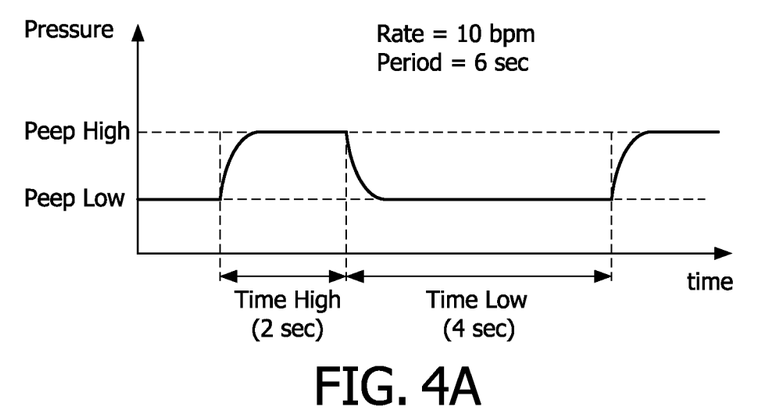
Figure 4B:
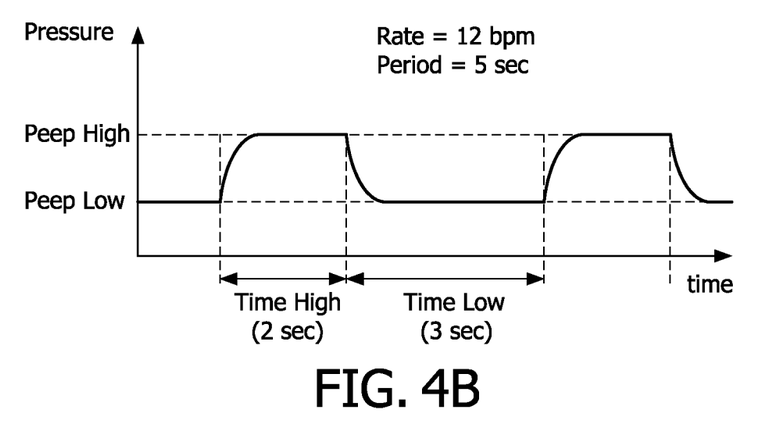

FIG. 4A shows example APRV therapy provided by the pressure supportH system 50 in a case where Time Low equals 4 seconds, Time High equals 2 seconds, the respiratory rate is 10 bpm, and the respiratory period is 6 seconds. In this example, Time Low is greater than Time High, and therefore, when apnea is detected, processing will proceed in accordance with steps 145-170 in FIG. 2B. FIG. 4B illustrates the apnea back-up mode that will follow the therapy shown in FIG. 4A when the predetermined apnea back-up rate is set to 12 bpm, resulting in an apnea period of 5 seconds. As seen in FIG. 4B, when apnea is detected, it is possible to achieve the apnea period of 5 seconds by only shortening Time Low of FIG. 4A while keeping Time Low greater than or equal to Time High. Thus, in the apnea back-up mode shown in FIG. 4B, Time Low is shortened to 3 seconds, and Time High is unchanged, resulting in a back-up therapy at the apnea rate/apnea period wherein the particular PEEP High and Low levels of the original APRV mode are maintained (see steps 150 and 155 of FIG. 2B).

Figure 4C:
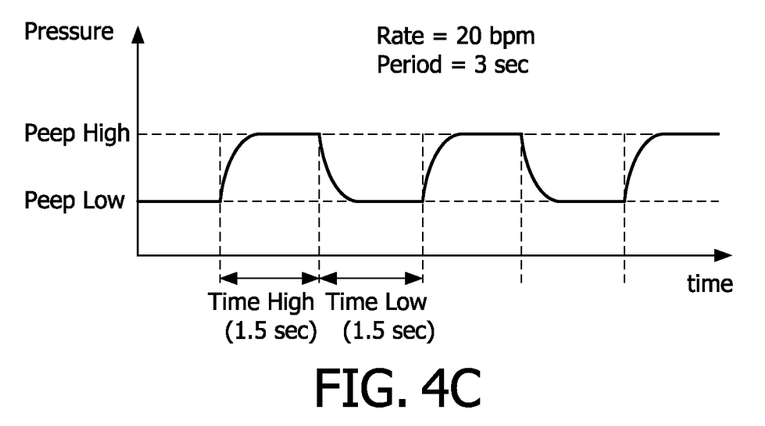

FIG. 4C illustrates the apnea back-up mode that will follow the therapy shown in FIG. 4A when the predetermined apnea back-up rate is set to 20 bpm, resulting in an apnea period of 3 seconds. As seen in FIG. 4C, when apnea is detected, it is not possible to achieve the apnea period of 3 seconds by only shortening Time Low of FIG. 4A while keeping Time Low greater than or equal to Time High. Thus, in this case, Time Low is first reduced to 2 seconds to make it equal to Time High. Then, both Time Low and Time High are reduced by 0.5 seconds so that each equals 1.5 seconds. This will result in a back-up therapy at the apnea rate/apnea period wherein the particular PEEP High and Low levels of the original APRV mode are maintained (see steps 160, 165 and 170 of FIG. 2A). Also, Time Low, which was originally longer than Time High, will remain at least greater than or equal to Time High in the back-up therapy that is provided.

Figure 5:
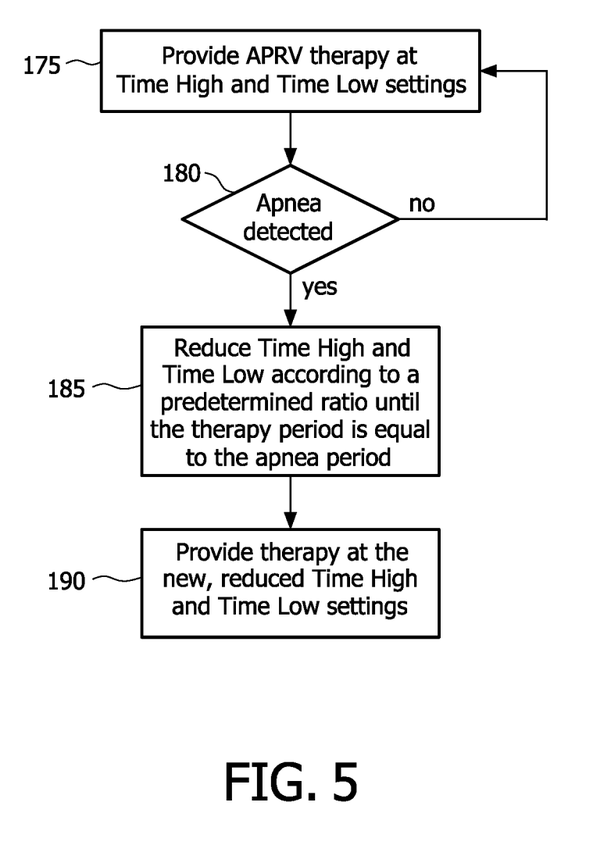
FIG. 5 is a flowchart of a method of providing apnea back-up ventilation according to an alternative particular, non-limiting embodiment of the invention.

FIG. 5 is a flowchart of a method of providing apnea back-up ventilation using pressure support system 50 according to an alternative particular, non-limiting embodiment of the invention. The method begins at step 175, wherein APRV therapy is provided to the patient 54 at predetermined PEEP High/Time High and PEEP Low/Time Low settings. Such settings may be established and input into the pressure support system 50 using the input/output device 66. Next, at step 180, a determination is made as to whether apnea is detected based on the pre-set apnea interval. Specifically, step 180 (like step 105 in FIG. 2A) determines whether no triggered breaths have been sensed during the pre-set apnea interval. If the answer at step 180 is no, then the method returns to step 175, where the original APRV therapy is continued. If, however, the answer at step 180 is yes, meaning that apnea has been detected, then, at step 185, Time High and Time Low are reduced according to a predetermined ratio until the therapy period is equal to the apnea period. In one particular embodiment, the predetermined ratio is equal to the ratio of original Time High to original Time Low, such that Time High and Time Low are reduced proportionally until the therapy period is equal to the apnea period.

In another, alternative particular embodiment, the predetermined ratio is 1:1, so that Time High and Time Low are reduced by equal amounts until the therapy period is equal to the apnea period. As was the case in FIGS. 2A and 2B, these specific ratios are meant to be exemplary only, and it will be understood that other ratios may be used and may be selectively set by a clinician or the patient as desired using the input/output device 66 of the pressure support system 50. Following step 185, the method proceeds to step 190, wherein therapy is provided at the original PEEP High and PEEP Low pressure levels at the new reduced Time High setting and the new reduced Time Low setting.

Figure 6A:
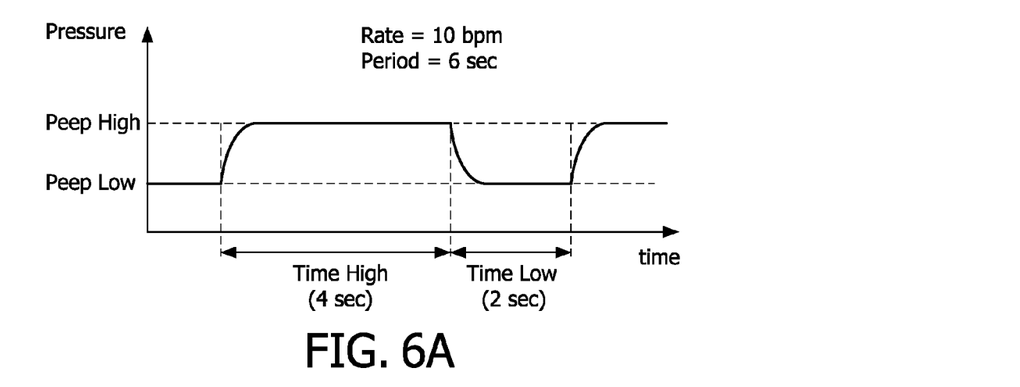
FIGS. 6A, 6B, and 6C show example pressure curves for therapy provided according to the method of FIG. 5.
Figure 6B:
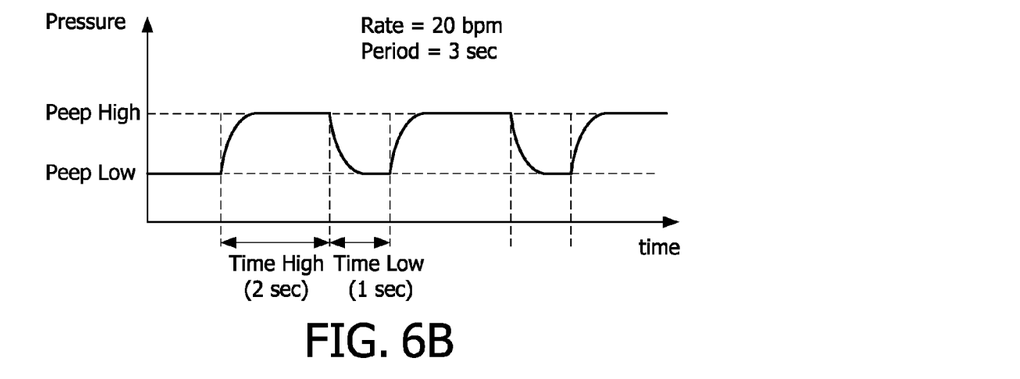
Figure 6C:
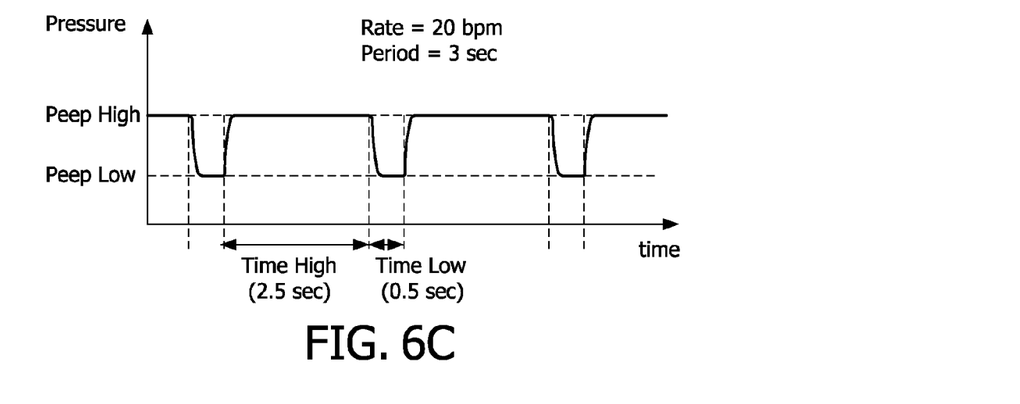

FIGS. 6A, 6B, and 6C show example pressure curves for therapy provided according to the method of FIG. 5. FIG. 6A shows example APRV therapy provided by the pressure support system 50 in a case where Time High equals 4 seconds, Time Low equals 2 seconds, the respiratory rate is 10 bpm, and the respiratory period is 6 seconds. FIG. 6B illustrates the apnea back-up mode that will follow the therapy shown in FIG. 6A when the predetermined apnea back-up rate is set to 20 bpm, resulting in an apnea period of 3 seconds, and when the ratio to be used in step 185 is equal to the ratio of original Time High to original Time Low.

As seen in FIG. 6B, when apnea is detected, both Time High and Time Low are reduced proportionally (Time High by 2 seconds and Time Low by 1 second) so that Time High equals 2 seconds and Time Low equals 1 second. This will result in a back-up therapy at the apnea rate/apnea period wherein the particular PEEP High and Low levels of the original APRV mode are maintained. FIG. 6C illustrates the apnea back-up mode that will follow the therapy shown in FIG. 6A when the predetermined apnea back-up rate is set to 20 bpm, resulting in an apnea period of 3 seconds, and when the ratio to be used in step 185 is 1:1.

As seen in FIG. 6C, when apnea is detected, both Time High and Time Low are reduced by equal amounts (1.5 seconds) so that Time High equals 2.5 seconds and Time Low equals 0.5 seconds. This will similarly result in a back-up therapy at the apnea rate/apnea period wherein the particular PEEP High and Low levels of the original APRV mode are maintained. While the therapy periods of the curves shown in FIGS. 6B and 6C are the same (3 seconds), the relative duration of Time High and Time Low differs between the two curves.

In any of the embodiments described herein, the apnea back-up therapy is provided until the patient is no longer apneic as indicated by the detection of patient initiated breaths within a predetermined apnea interval.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of providing pressure support to a patient, comprising:
    delivering a first flow of breathing gas to the patient the first flow of breathing gas having a first positive pressure level and a second positive pressure level, the first and second positive pressure levels alternating with on another in a plurality of first cycles in the first flow of breathing gas, the first flow of breathing gas having a first period that is different than a predetermined apnea period;
    determining that the patient is experiencing an apineic episode; and
    delivering, responsive to a determination that the patient is experiencing an apneic event, a second flow of breathing gas to the patient, the second flow of breathing gas having the first positive pressure level and the second positive pressure level, the first and the second positive pressure levels alternating with one another in a plurality of second cycles in the second flow of breathing gas, the second flow of breathing gas having a second period that is equal to the predetermined apnea period.

2. The method according to claim 1, wherein in first flow of breathing gas the first positive pressure le el in each of the first cycles has a first duration and the second positive pressure level in each of the first cycles has a second duration, the first duration being longer than the second duration, and wherein the second flow of breathing gas the first positive press re level in each of the second cycles has a third duration that is less than the first duration and the second positive pressure level in each of the second cycles has the second duration.

3. The method according to claim 1, wherein in the first flow of breathing gas the first positive pressure level in each of the first cycles has a first duration and the second positive pressure level in each of the first cycles has a second duration, the first duration being longer than the second duration, and wherein in the second flow of breathing gas the first positive pressure level in each of the second cycles has a third duration that is less than the first duration and the second positive pressure level each of the second cycles has a fourth duration that is less than he second duration.

4. The method according to claim therein the third duration is equal or loner than the fourth duration.

5. The method according to claim 3, wherein the third duration and the fourth duration are determined by first reducing the first duration to equal the second duration and then reducing the first duration and the second duration according to a predetermined ratio to equal the third duration and the fourth duration, respectively.

6. The method according to claim 5, wherein the predetermined ratio is 1:1 or is a ratio of the first duration to the second duration.

7. The method according to claim 3, wherein the third duration and the fourth duration are determined by reducing the first duration and the second duration according to a predetermined ratio to equal the third du and the fourth duration, respectively.

8. The method according to claim 7 wherein the predetermined ratio is 1:1 or is a ratio of the first duration to the second duration.

9. The method according to claim 1, wherein in the first flow of breathing gas the first positive pressure level in each of the first cycles has a first duration and the second positive pressure level in each of the first cycles has a second duration, the first duration being longer than the second duration and wherein in the second flow of breathing gas the first positive pressure level in each of the second cycles has a third duration and the second positive pressure level in each of the second cycles has a fourth duration, the third duration being longer than the fourth duration.

10. A pressure support system, comprising
    a pressure generating system;
    a patient circuit operatively coupled to the pressure generating system; and
    a controller operatively coupled to the pressure generating system, the controller being adapted to: (i) control the pressure generating system to deliver a first flow of breathing gas to the patient through the patient circuit, the first flow of breathing gas having a first positive pressure, level and a second positive pressure level, the first and second positive pressure levels alternating with one another in a plurality of first cycles in the first flow of breathing gas, the first flow of breathing gas having a first period that is different than a predetermined apnea period, (ii) determine that the patient is experiencing an apneic episode, and (iii) in response to determining that the patient is experiencing an apneic episode, control the pressure generating system to deliver a second flow of breathing gas to the patient, the second flow of breathing gas having the first positive pressure level and the second positive pressure level, the first and second positive pressure levels alternating with one another in a plurality of second cycles in the second flow of breathing gas, the second flow of breathing as having a second period that is equal to the predetermined apnea period.

11. The pressure support system according to claim 10, wherein in the first flow of breathing gas the first positive pressure level in each of the first cycles has a first duration and the second positive pressure level in each of the first cycles has a second duration, the first duration being longer than the second duration, and wherein in the second flow of breathing gas the first positive pressure level in each of the second cycles has a third duration that is less than the first duration and the second positive pressure level in each of the second cycles has the second duration.

12. The pressure support system according to claim 10, herein in the first flow of breathing gas the first positive pressure level in each of the first cycles has a first duration and the second positive pressure level in each of the first cycles has a second duration, the first duration being longer than the second duration, and wherein in the second flow of breathing gas the first positive pressure level in each of the second cycles has a third duration that is less than the first duration and the second positive pressure level in each of the second cycles has a fourth duration that is less than the second duration.

13. The pressure support system according to claim 12, wherein the third duration is equal to or longer than the fourth duration.

14. The pressure support system according to claim 12, wherein the third duration and the fourth duration are determined by first reducing the first duration to equal the second duration and then reducing the first duration and the second duration according to a predetermined ratio to equal the third duration and the fourth duration, respectively.

15. The pressure support system according to claim 14, wherein the predetermined ratio is 1:1 or is a ratio of the first duration to the second duration.

16. The pressure support system according to claim 12, wherein the third duration and the fourth duration are determined by reducing the first duration and the second duration according to a predetermined ratio to equal the third duration and the fourth duration, respectively.

17. The pressure support system according to claim 16 wherein the predetermined ratio is 1:1 a ratio of the first duration to the second duration.

18. The pressure support system according to claim 12, wherein in the first flow of breathing gas the first positive pressure level in each he first cycles has a first duration and the second positive pressure level in each of the first cycles has a second duration the first duration being longer than the second duration, and wherein in the second flow of breathing gas the first positive pressure level in each of the second cycles has a third duration and the second positive pressure level in each of the second cycles has a fourth duration, the third duration being longer than the fourth duration.

* * * * *